(12) United States Patent
Bern

(10) Patent No.: US 9,671,408 B2
(45) Date of Patent: Jun. 6, 2017

(54) WILD-CARD-MODIFICATION SEARCH TECHNIQUE FOR PEPTIDE IDENTIFICATION

(75) Inventor: Marshall W. Bern, San Carlos, CA (US)

(73) Assignee: PROTEIN METRICS INC., San Carlos, CA (US)

( * ) Notice: Subject to any disclaimer, the term of this patent is extended or adjusted under 35 U.S.C. 154(b) by 1821 days.

(21) Appl. No.: 12/272,973

(22) Filed: Nov. 18, 2008

(65) Prior Publication Data

US 2010/0124785 A1    May 20, 2010

(51) Int. Cl.
*G01N 33/00* (2006.01)
*G06F 9/06* (2006.01)
*G01N 33/68* (2006.01)

(52) U.S. Cl.
CPC .............................. *G01N 33/6848* (2013.01)

(58) Field of Classification Search
CPC  G06F 19/10; G06F 19/16; H01J 49/36; H01J 49/45
See application file for complete search history.

(56) References Cited

U.S. PATENT DOCUMENTS

| 5,538,897 | A * | 7/1996 | Yates et al. ...................... 436/89 |
| 2003/0028932 | A1 * | 2/2003 | Skilling ........................... 930/10 |
| 2005/0192755 | A1 * | 9/2005 | Nagalla et al. .................. 702/19 |
| 2007/0282537 | A1 * | 12/2007 | Freitas et al. ................... 702/19 |
| 2010/0057372 | A1 * | 3/2010 | Fagerquist et al. ............. 702/20 |

OTHER PUBLICATIONS

Cagney et al. Proteome Science 2003, 1:5, pp. 1-15. http://www.Proteomesci.com/content/1/1/5.*
Colinge et al. Database CaPlus, DN 144:327333 (Journal of Proteome Research (2006), 5(3), 619-624). See CaPlus Abstract.*
Bandeira et al. PNAS, Apr. 2007, vol. 104 No. 15, p. 6140-6145.*
Prospector General Instructions, "Instructions for General Features Common to Multiple Protein Prospector Programs", downloaded Sep. 15, 2009, http://prospector.ucsf.edu/prospector/html/instruct/allman.htm.

* cited by examiner

*Primary Examiner* — Michael Borin
(74) *Attorney, Agent, or Firm* — Shun Yao; Park, Vaughan, Fleming & Dowler LLP

(57) ABSTRACT

Embodiments of a computer system, a method, and a computer-program product (e.g., software) for analyzing tandem-mass-spectrometry data are described. Using this analysis technique, unanticipated chemical modifications to peptides associated with proteins can be identified. In particular, a modification called a wild-card modification is used to identify the most likely chemical modifications in the peptides. A wild-card modification allows the addition of any mass, typically any integer atomic mass within a range, to any one amino acid residue within a candidate peptide.

20 Claims, 4 Drawing Sheets

WILD-CARD-MODIFICATION SEARCH TECHNIQUE FOR PEPTIDE IDENTIFICATION

BACKGROUND

Field of the Invention

The present invention relates to techniques for analyzing mass-spectrometry data. More specifically, the present invention relates to the analysis of mass-spectrometry data for peptides.

Related Art

In proteomics, proteins are often identified using mass spectrometry. A protein sample is typically digested into peptides that include one or more amino acids. For example, the protein sample can be digested using the enzyme trypsin. The resulting peptides can be ionized using matrix assisted laser desorption ionization or electro-spray ionization and introduced into a mass spectrometer. Tandem mass spectrometry measures the mass-to-charge ratios of the peptides, and then fragments the peptides and measures the mass-to-charge ratio of the resulting fragments. Peptide identifications made from tandem-mass-spectrometry data can be aggregated to identify the proteins in the sample.

In principle, the peptides in the sample can be uniquely identified using the peaks in the resulting mass-spectrometry spectra (which are associated with the mass-to-charge ratios of the peptides and peptide fragments). For example, peptides may be identified by comparing the observed mass-spectrometry spectra to theoretical mass-spectrometry spectra of peptides predicted by gene sequences or to previously observed mass-spectrometry spectra for known peptides.

In practice, however, it is often difficult to identify the peptides. For example, there may be chemical modifications to the amino acids in the peptides. These chemical modifications may be in vivo post-translational modifications or simply chemical artifacts, such as modifications that occur when the protein sample is prepared for mass-spectrometry analysis. When present, the chemical modifications can lead to shifts in the peaks in the mass-spectrometry spectrum of a peptide, which can complicate or confound the identification of the peptide based on comparisons with the previously observed or theoretically predicted mass-spectrometry spectra for known peptides.

One existing analysis technique attempts to address this problem by shifting some or all of the peaks in the previously observed or theoretically predicted mass-spectrometry spectra, based on one or more chemical modifications that are anticipated (prior to the mass-spectrometry analysis) to occur in the protein sample. The mass-spectrometry spectra with shifted peaks can then be compared with the observed unknown mass-spectrometry spectrum in order to make an identification. Unfortunately, the chemical modifications in a protein sample are difficult to guess a priori. Moreover there are more than 200 types of potential chemical modifications, and ten or more of these types may be present in a single protein sample, so it is often too computationally expensive to search for all combinations of all potential modifications. Consequently, this existing analysis technique may be too restrictive to properly analyze the observed mass-spectrometry spectra.

Another existing analysis technique uses a so-called "blind modification search" to identify the peptide represented in an observed mass-spectrometry spectrum. In this existing analysis technique, peaks in the observed mass-spectrometry spectrum are fit without using any prior knowledge of likely mass shifts, apart from upper and lower bounds on the size of the shift. Blind modification search, however, is often too general because it does not take advantage of chemical knowledge, such as the propensity of methionine to oxidize, or the likelihood of chemical artifacts at the peptide N-terminus.

Hence, what is needed is a method and an apparatus that facilitates analysis of mass-spectrometry data for proteins without the problems listed above.

SUMMARY

One embodiment of the present invention provides a computer system to identify potential modifications to peptides associated with a protein sample. During operation, the computer system accesses mass-spectrometry data, which includes measured tandem-mass-spectrometry spectra and a corresponding measured precursor mass for each tandem spectrum. The computer system also accesses a protein database containing amino acid sequences for a set of proteins or peptides. Then, the computer system matches candidate peptides from the protein database to the mass-spectrometry data by generating theoretical tandem mass-spectrometry spectra for some or all of the candidate peptides and comparing them to the observed, but not yet identified, tandem mass-spectrometry spectra. For example, a theoretical mass-spectrometry spectrum for a candidate peptide without any chemical modifications can be computed by including peaks in the theoretical spectrum which correspond to fragments of the amino acid sequence of the candidate peptide. However, a theoretical spectrum of a candidate peptide with a modification includes peaks that are 'shifted' from their normal locations by a mass equal to the mass of the modification. For a given candidate peptide and a given observed mass-spectrometry spectrum, the computer system deduces the approximate magnitude of the peak shift (if indeed the candidate peptide is the peptide in the spectrum) from the theoretical mass of the given candidate peptide and the given observed precursor mass of the observed spectrum. In particular, the peak shift equals the 'missing mass,' i.e., the difference between the theoretical mass of the given candidate peptide and the observed precursor mass of the given observed mass-spectrometry spectrum.

Given a maximum allowed peak shift (such as, 100 Daltons) and a minimum allowed peak shift (such as, −30 Daltons), which may be specified by a user, the allowed peak shifts may correspond to all integers in the range between the minimum and the maximum allowed peak shifts. Note that the allowed peak shifts may, in turn, limit the candidate peptides that are considered for any given observed tandem mass-spectrometry spectrum. For example, if the precursor mass of the observed spectrum is 1000 Daltons, and the peak shift range is between −30 and 100 Daltons, then candidate peptides with masses between 900 and 1030 Daltons may be considered. A candidate peptide with a theoretical mass of 960 Daltons may be assumed to have a peak shift corresponding to a mass of 40 Daltons, i.e., the amount of the missing mass. Moreover, there may be a range for the precursor mass (for example, 998 to 1002 Daltons), in which case a candidate peptide with theoretical mass 960 Daltons may be checked with peak shifts corresponding to masses of 38, 39, 40, 41, and 42 Daltons.

Furthermore, the peak shift may be applied to various sets of peaks in the theoretical mass-spectrometry spectrum of the candidate peptide, and each set of peaks may correspond to a location for a chemical modification within the candidate peptide. For example, a chemical modification to the third amino acid residue in a 10-residue peptide may shift each peak corresponding to an ion containing the third amino acid residue, but may not shift a peak corresponding to an ion that does not contain the third amino acid residue.

Additionally, the given set of candidate peptides may include candidate peptides with known chemical modifications. For example, the candidate peptide may include one oxidized methionine (which has a mass of approximately 147 Daltons) replacing one unmodified methionine (which has a mass of approximately 131 Daltons). This known chemical modification results in a peak shift of approximately 16 Daltons for all the mass-spectrometry peaks corresponding to ions containing the oxidized methionine. Note that the shift associated with the known chemical modification is distinct from the peak shift caused by an unknown modification, and a theoretical ion that includes both known and unknown modifications gives a theoretical peak at a location shifted by the sum of these two types of shifts. Note that the unknown modification is called a "wild-card modification," because it can match any mass addition or subtraction (which may be an integer or a non-integer within a range of masses) at any location within the peptide.

In some embodiments, the one or more known modifications may include natural modifications, such as: methylation, dimethylation, oxidation, phosphorylation and/or acetylation, as well as deliberate chemical treatments such as isotope labeling, lysine, cysteine and/or N-terminal modifications. Unlike wild-card modifications, known modifications result in known (predetermined) mass shifts, which are the same for all candidate peptides. In addition, most known modifications apply to certain amino-acid residues or certain positions within a peptide. For example, N-terminal methylation adds +14 Daltons to the N-terminal residue in a peptide, while oxidized methionine adds +16 Daltons to one or more methionine residues within a peptide.

In some embodiments, the computer system compares the measured mass-spectrometry peak locations with expected mass-spectrometry peak locations for a candidate peptide prior to comparing the measured precursor mass with the theoretical mass of the candidate peptide. This order of comparison may decrease the time needed to identify one or more candidate peptides corresponding to the potential modifications.

In some embodiments, identifying the potential modifications to the peptides may involve an iterative process, in which the unknown, wild-card modifications identified in a given iteration are treated as known modifications in a subsequent iteration.

Another embodiment provides a method including at least some of the above-described operations.

Another embodiment provides a computer-program product for use in conjunction with the computer system.

BRIEF DESCRIPTION OF THE FIGURES

Note that like reference numerals refer to corresponding parts throughout the drawings.

DETAILED DESCRIPTION

Figure 1A:
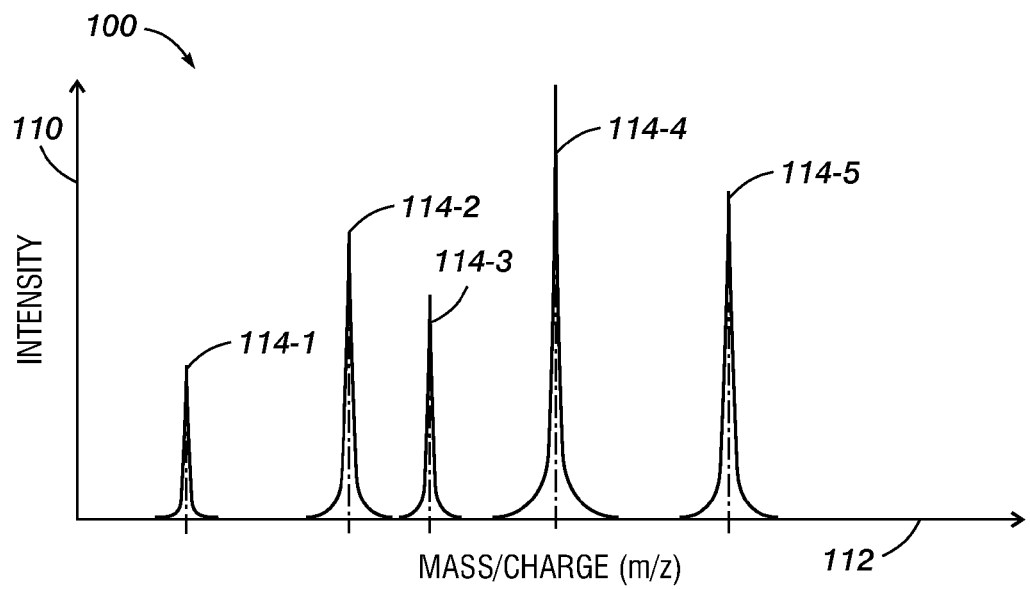
FIG. 1A is a graph illustrating a tandem-mass-spectrometry spectrum in accordance with an embodiment of the present invention.

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

Embodiments of a computer system, a method, and a computer-program product (e.g., software) for analyzing mass-spectrometry data are described. Using this analysis technique, unanticipated chemical modifications to peptides can be determined, which in turn allows proteins in a biological sample to be identified based on measured mass-spectrometry spectra. In particular, a single wild-card modification, along with a few common known modifications, may be used to identify the most-likely chemical modifications in the peptides. Note that a single wild-card modification applies one (typically integer) mass change to any one amino-acid residue in a given peptide. Moreover, in some embodiments, two wild-card modifications apply separate mass changes to an arbitrary pair of amino-acid residues in the given peptide.

By considering multiple known chemical modifications while simultaneously allowing at least one unknown modification in the given peptide, this analysis technique strikes a balance between techniques that are too rigid and those that are too flexible. This analysis technique also enables direct comparison of searches with and without the allowance of an unknown modification in order to assess the statistical significance of the unknown-modification identification. Consequently, this technique can reduce the time and cost associated with the analysis of mass-spectrometry data.

We now discuss embodiments of an analysis technique to identify one or more potential chemical modifications to peptides associated with a protein. During tandem mass spectrometry, a fragmentation spectrum is generated. This spectrum includes spectral peaks corresponding to fragments of a precursor (or "parent") ion, which includes molecular subunits that are connected at cleavage sites. In particular, in a first stage of the tandem mass spectrometer, charged molecules (the parent ions) that have approximately the same ratio of mass-to-charge (m/z) are selected (typically, within a narrow tolerance). Then, in a second stage of the tandem mass spectrometer, the selected parent ions are fragmented at cleavage sites. These fragments are accumulated in m/z histogram bins. A number of these bins can represent a single spectral peak in a mass-spectrometry spectrum. Moreover, the number of counts in a given spectral peak (i.e., the height), the area under the given spectral peak, or a combination of the height and area of the spectral peak can be used to calculate the intensity of the given spectral peak. Note that the charge z for the fragments of the parent ion is typically 1, so that the position along the x-axis in the mass-spectrometry spectrum corresponds directly to mass for most peaks.

FIG. 1A presents a graph illustrating a mass-spectrometry spectrum 100 of a parent ion plotted as intensity 110 as a function of m/z 112. In this mass-spectrometry spectrum, peaks at peak locations 114 are associated with fragments of the parent ion(s) that have specific masses. In some embodiments, the parent ion is: a protein, a peptide (i.e., a portion of a protein), a lipid, a polymer (which is composed of multiple monomers), a glycan, and/or another organic compound or molecule.

For example, the parent ion may be a peptide and the fragments of the parent ion are smaller peptides. The parent peptide includes a sequence of amino-acid residues that are connected by peptide bonds, which are likely cleavage sites. A pair of fragments that are dissociated by a tandem mass spectrometer may be created by breaking the parent peptide at a given cleavage site. Thus, if the peptide includes the amino-acid sequence alanine-methionine-cysteine-aspartic acid-glutamic acid (AMCDE), the fragments may include: A, MCDE, AM, CDE, AMC, DE, AMCD, and/or E. Moreover, the intensity 110 of the corresponding spectral peaks in mass-spectrometry spectrum 100 may indicate how often the parent ion(s) have been fragmented at a particular cleavage site.

Figure 1B:
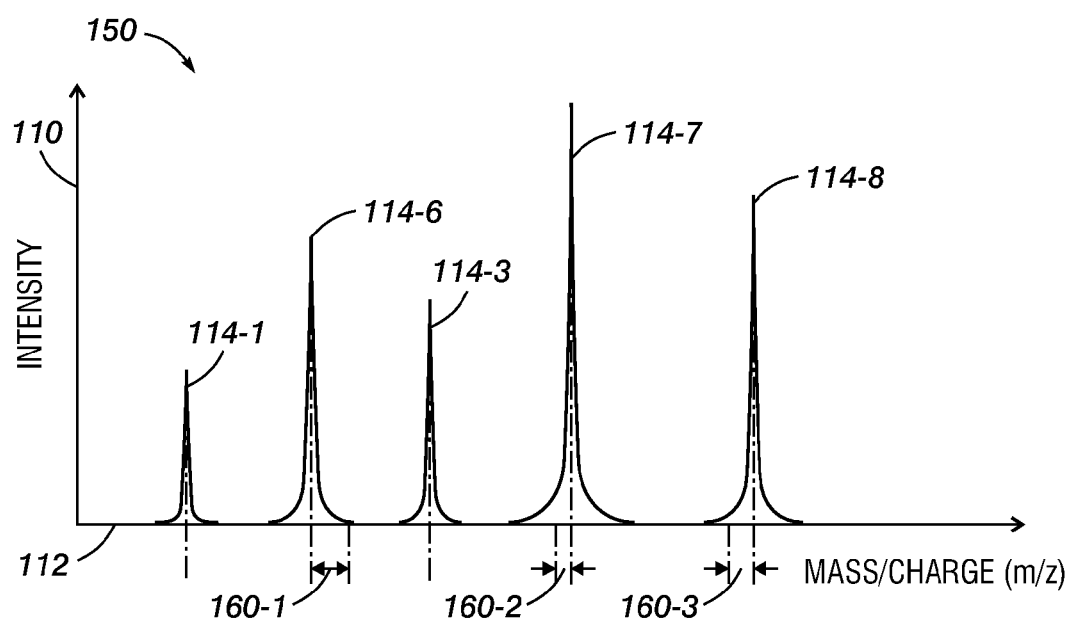
FIG. 1B is a graph illustrating a tandem-mass-spectrometry spectrum in accordance with an embodiment of the present invention.

For peptides and proteins, it can be difficult to identify a particular peptide or protein from the peak locations 114. One source of this difficulty is chemical modification of amino-acid residues in the peptide. As shown in FIG. 1B, which presents a graph illustrating a mass-spectrometry spectrum 150, these chemical modifications result in shifts 160 of some of the peak locations 114 (such as peak locations 114-6, 114-7 and 114-8) that are associated with affected amino acids.

For example, M in the peptide AMCDE may be oxidized, which results in a mass shift of all of the peak locations 114 that are associated with fragments that include M (i.e., the peak locations associated with MCDE, AM, AMC and/or AMCD, which include half of the fragments). These peaks may all be shifted by the same amount (+16 Daltons in the case of oxidized methionine), while the remainder of the peaks may be at their original theoretical peak locations.

If the chemical modification(s) of the amino acids in the protein sample are known (prior to the mass-spectrometry analysis), then software such as the peptide identification programs Mascot (from Matrix Science, Inc., of Boston, Mass.) and SEQUEST (from Sage-N Research, Inc., of San Jose, Calif.) can be instructed to search for peptides that include the chemical modification(s) and which match the peak locations 114 (which is referred to as a "known" modification search). In this way, modified peptides can be identified.

Unfortunately, the chemical modification(s) to the peptides or proteins in the sample are not all known in advance. Moreover, there are 100 or more possible types of chemical modifications (such as methylation, dimethylation, oxidation, deamidation, carbamylation, phosphorylation or acetylation), and as many as five to ten of these types may be present in a given protein sample. Note that the chemical modifications present typically depend on both the biological system and on the chemical processing of the protein sample. Some modifications such as oxidized methionine, pyro-glu transformation of N-terminal glutamine or aspartic acid, and deamidation of glutamine and asparagine are ubiquitous, found in almost every sample, whereas some other modifications are found only in certain samples. Searching for all the mass shifts that occur in a given sample without knowledge of the common chemical modifications (using a so-called "blind search") is extremely time consuming and error-prone, and produces results that can be hard to interpret.

In the discussion that follows, this problem is addressed using a wild-card-modification analysis or search technique, which considers a range of potential mass shifts (typically integer) to amino acid residues in one or more fragments of a peptide or a protein. Note that a wild-card modification can be enabled along with any combination of known modifications. This type of search allows users to build in knowledge of the modifications already known or which are suspected to occur in the protein sample. Thus, the search does not waste time or make errors in discovering something that is already known, such as the propensity of methionine to oxidize. By more selectively choosing the potential chemical modifications considered per peptide, the wild-card-modification technique allows faster, cheaper and more accurate identification of the peptide or protein sample being analyzed than other search techniques. Moreover, candidate identifications using wild-card modifications can be compared directly with candidate identifications using only known modifications, so that the strength of evidence for the unknown modification can be assessed statistically.

One embodiment of wild-card-modification search allows "any" integer mass shift on any one residue within each candidate peptide. More precisely, the considered mass additions or subtractions are exactly those additions or subtractions of integer masses that, along with the assumed known modifications, yield a total mass for the candidate peptide within the considered precursor mass range. Moreover, in some embodiments, the wild-card modification is restricted to certain amino-acid residues or to the N-terminal or C-terminal residue within each peptide.

Another embodiment, designed for high-accuracy tandem mass spectrometry (such as Fourier-transform mass spectrometry or quadrupole time-of-flight mass spectrometry), allows mass additions and subtractions that are not an integer number of Daltons (atomic mass units). For example, if the precursor mass is known to be 1290.76+/−0.01 Daltons, and the candidate peptide EKAEGDAALNR without a wild-card modification has theoretical mass 1272.66 Daltons, then the wild-card-modification search may include only additions of 18.10 Daltons, that is, the candidates E[+18.10 Daltons]KAEGDAALNR, EK[+18.10 Daltons] AEGDAALNR, and so forth.

Figure 2:
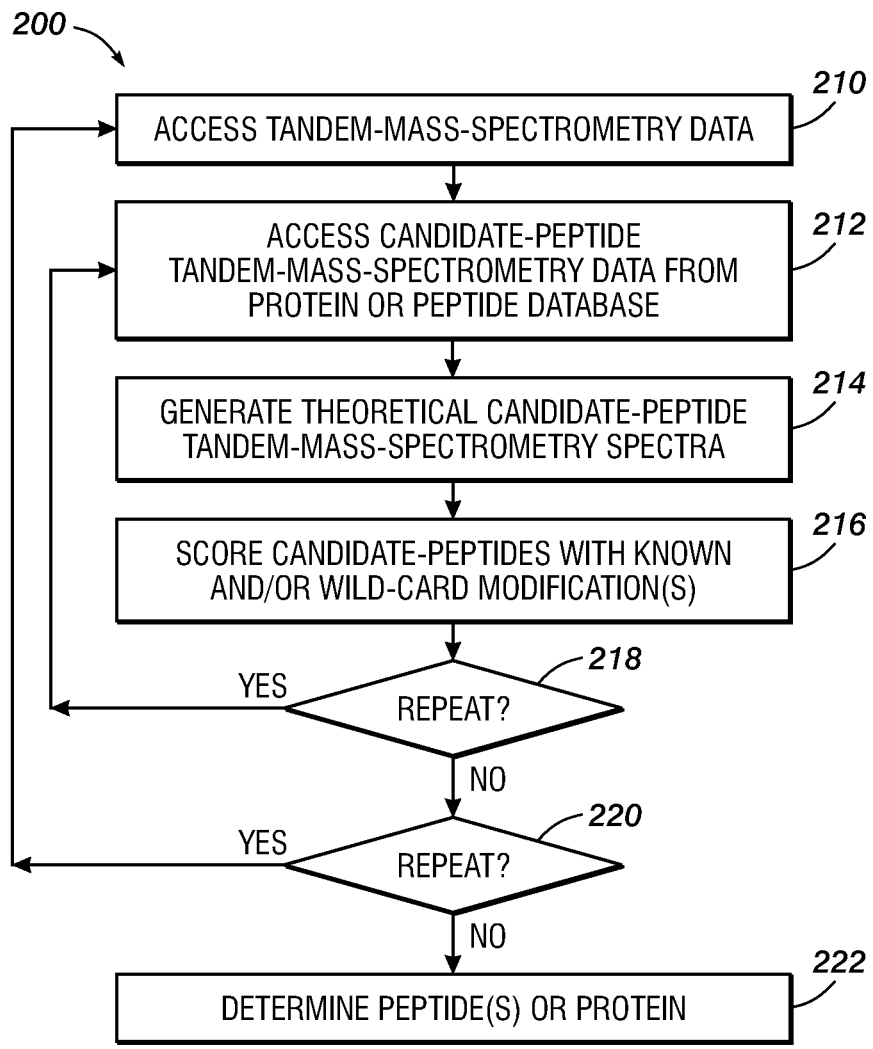
FIG. 2 is a flow chart illustrating a process for identifying one or more potential modifications to peptides associated with a protein in accordance with an embodiment of the present invention.

FIG. 2 presents a flow chart illustrating a process 200 for identifying peptides associated with a protein sample. The process may be performed by a computer system. During operation, the computer system accesses tandem-mass-spectrometry data, which includes precursor masses (masses of the unfragmented peptides) along with fragmentation spectra (210).

In process 200, there are two loops. An outer loop over all tandem-mass-spectrometry spectra (including precursor masses with an associated uncertainty k), and an inner loop over all candidate peptides. For a given tandem-mass-spectrometry spectrum s, the computer system accesses candidate-peptide tandem-mass-spectrometry data from a protein or peptide database (212). Note that a given candidate-peptide tandem-mass-spectrometry spectrum p in this data includes a theoretical mass which is within a user-defined tolerance of the precursor mass. Moreover, the difference between the theoretical mass and the precursor mass defines a maximum mass difference.

Then, the computer system generates theoretical candidate-peptide tandem-mass-spectrometry spectra (214), which include known modifications (having known shifts corresponding to associated known masses) and/or a range of wild-card modifications (having associated variable shifts corresponding to masses in the range), which are applied to one or more particular amino-acid residues in a given theoretical candidate-peptide tandem-mass-spectrometry spectrum. Note that the magnitude of the total shifts associated with the combination of these modifications (wherein a combination can include at least one wild-card modification and zero or more known modifications) are less than a shift corresponding to the maximum mass difference between the theoretical and measured total mass values for a given peptide.

In one embodiment, the computer system allows a user to determine how to combine the modifications. That is, a user can designate zero or more known modifications to be combined with a wild-card modification, and also designate one or more amino acids to apply the combined modification. Since the wild-card modification can vary the mass shift within the given range, the computer system can iteratively traverse all possible wild-card modifications within that range. Subsequently, the computer system scores the candidate peptides with known and/or wild-card modifications (216). This way, the computer system can identify a modification that results in the closest match with the measured spectrometry data.

The computer system may optionally repeat (218) operations 212-216 for one or more additional candidate peptides and/or may optionally repeat (220) operations 212-218 for one or more additional tandem-mass-spectrometry spectra. Based on the identified potential modifications, the computer system may determine (222) one or more peptide(s) and/or proteins that match the protein sample(s) which correspond to the tandem-mass-spectrometry spectra.

In particular, the computer system may access a database of known peptides or proteins. For each tandem mass-spectrometry spectrum, the computer may assemble: a list of candidate peptides, based upon the precursor mass associated with the tandem-mass-spectrometry spectrum; the locations of peaks within the tandem mass-spectrometry spectrum; and/or a "sequence tag" (partial amino acid sequence) deduced de novo from the tandem mass-spectrometry spectrum, a priori knowledge of the protein sample, or any other information relevant to the selection of candidate peptides.

For each tandem mass-spectrometry spectrum, the computer system may then evaluate how well each candidate peptide, and each modified version of each candidate peptide, explains the precursor mass and the peaks in the tandem mass-spectrometry spectrum. For example, assume that a tandem mass-spectrometry spectrum has a precursor mass known to lie in the range 578 to 580 Daltons. The unmodified candidate peptide AMCDE, along with one proton to give it charge, has a mass of approximately 550 Daltons, so it can be rejected because its mass lies outside the precursor mass range. However, the same candidate carrying one or more modifications is still a viable explanation. For example, AM[+30 Daltons]CDE denotes the same peptide with an additional mass of 30 Daltons attached to methionine, giving a total mass of 580 Daltons, which is within the required precursor mass range. Note that the additional mass shifts all the peaks corresponding to fragment ions containing methionine by 30 Daltons, so this explanation can be evaluated by checking the tandem mass-spectrometry spectrum for peaks corresponding to masses of: 233 Daltons (the mass of AM[+30 Daltons] along with one proton), 336 Daltons (the mass of AM[+30 Daltons]C along with one proton), and so forth. Evaluating an explanation for a tandem mass-spectrometry spectrum is called "peptide scoring." Peptide scoring is familiar to anyone skilled in the art, but for completeness this process is described in more detail below. Some embodiments may evaluate an explanation by checking fragment peaks before the parent mass, rather than the parent mass before fragment peaks as described here. Other embodiments may bring additional information into the evaluation of the explanation, for example, the identity of the protein(s) containing the candidate peptide.

Continuing with the same example, A[+14 Daltons]M[+16 Daltons]CDE denotes the peptide AMCDE with an additional 14 Daltons attached to alanine and an additional 16 Daltons attached to methionine, which (along with a proton) again gives a total mass of 580 Daltons. A known-modification search may allow only oxidized methionine modifications. This search considers AMCDE and AM[+16 Daltons]CDE (which includes an oxidized methionine) and may reject them both on the grounds of incorrect parent mass. A blind-modification search (as can be performed by the Popitam method, described by Hernandez et al., Proteomics, Vol 3, No. 6, 2003, 870-878, or by InsPecT, described by Tsur et al., Nature Biotechnology, Vol. 23, 1562-1567) may allow one or more arbitrary mass shifts, and thus may evaluate explanations such as: A[+28 Daltons]MCDE, A[+29 Daltons]MCDE, A[+30 Daltons]MCDE, A[+10 Daltons]M[+18 Daltons]CDE, A[+10 Daltons]M[+10 Daltons]C[+8 Daltons]DE, and so forth.

A wild-card modification search may allow oxidized methionine along with one wild-card modification. This search may evaluate: A[+28 Daltons]MCDE, A[+29 Daltons]MCDE, and A[+30 Daltons]MCDE, but may not evaluate A[+10 Daltons]M[+18 Daltons]CDE. However, it may evaluate A[+14 Daltons]M[+16 Daltons]CDE with the [+14 Daltons] coming from the wild-card modification and the [+16 Daltons] coming from the known modification. This explanation is in fact chemically plausible, and the wild-card-modification search may find it, without having to consider as many implausible explanations (such as A[+10 Daltons]M[+18 Daltons]CDE) as may be considered by blind-modification search.

Explanations with wild-card modifications can be generated systematically from the candidate peptide and the precursor mass range. For example, for the candidate peptide AMCDE (which has a mass of 550 Daltons) and the precursor mass range 578 to 580 Daltons, the computer system may try wild-card-modification masses of 28, 29, and 30 Daltons for each amino-acid residue. In this way, the mass of the candidate peptide with modifications (the "explanation") may fit the allowed precursor mass range. Similarly, the computer system may also generate explanations using known modifications, for example, AM[+16 Daltons]CDE (which has a mass of 566 Daltons), and then may fill in the missing mass with a wild-card modification (such as wild-card-modification masses of 12, 13, or 14 Daltons). In some embodiments, predetermined tables that give the combinations of known and wild-card modifications that sum to each integer mass are used. For example, the run time may be improved if it is known in advance that +30 Daltons can be formed by two known-modification +16 Daltons and one wild-card modification of −2 Daltons. Moreover, in some embodiments the total number of modifications per peptide is limited. For example, a limit of two known modifications and one wild-card modification may be defined.

In some embodiments, identifying the potential modifications to the peptides involves an iterative process, in which potential modifications identified in a given iteration are treated as known modifications (with fixed shifts) in a subsequent iteration. In the above example, an identification of A[+14 Daltons]M[+16 Daltons]CDE suggests that the protein sample may include N-terminal methylation, a known but unanticipated modification, which adds 14 Daltons to the first amino-acid residue in a peptide. This iterative process may allow chemical modifications that were missed during a previous iteration to be identified during a subsequent iteration. Thus, wild-card-modification search may enable a user to discover an optimal set of known modifications to use in the peptide or protein analysis.

Note that process 200 may include additional or fewer operations. Moreover, the order of the operations may be changed, and/or two or more operations may be combined into a single operation.

In an exemplary embodiment, an optional first pass at identification may be performed using a known search, which may include known (that is, anticipated) chemical modification(s). For example, at least some of the chemical modification(s) may be inferred based on how a protein sample was prepared. The optional first pass may be used to reduce the size of the relevant portion of the protein or peptide database, and thereby to speed up the wild-card-modification search. For example, a first pass may reduce 50,000 protein sequences (the size of a typical human protein database) down to 1000 protein sequences (roughly the maximum number of proteins that can be identified in a single mass-spectrometry experiment). This two-pass approach is based on the reasonable assumption that each protein may be represented by at least one peptide with no modifications or with only anticipated modifications.

Then, a wild-card-modification search may be performed. If the first pass found some known modifications, then the wild-card-modification search may include these known modifications. However, if the first pass did not find modifications, or if no first pass was performed, then the wild-card-modification search may include no modifications other than the wild card and/or deliberate modifications (such as cysteine treatment).

Scoring of candidate peptides with wild-card modifications (which are sometimes referred to as "explanations") may be similar to the peptide scoring performed by existing software programs such as Mascot, SEQUEST, and X!Tandem (from the Global Proteome Machine Organization). For example, the computer system may first compare the mass of an explanation with the observed precursor mass of the spectrum to be identified. The observed precursor mass may be derived from the observed precursor mass-over-charge using either an observed or presumed charge for the peptide. In most proteomics experiments, peptide charges are +1, +2, +3, or +4, so all four possibilities can be tried if the actual charge cannot be observed. Then, the computer system evaluates the explanation by generating a theoretical mass-spectrometry spectrum for the explanation. This theoretical mass-spectrometry spectrum may include peaks corresponding to expected ions. Note that expected ions are known to those skilled in the art, and include ions corresponding to prefixes and suffixes of the amino-acid residue sequence, such as a-, b-, and c-ions (three types of prefix ions) and y- and z-ions (two types of suffix ions). Expected ions may also include prefix and suffix ions associated with loss of water or ammonia. The scoring function may take into account the number or fraction of theoretical ions matched (within some mass tolerance) by peaks in the observed spectrum. Moreover, it may also take into account the number or fraction of peaks in the observed spectrum matched (within some mass tolerance) by theoretical ions. Furthermore, it may also take into account: the intensities of observed peaks, the predicted intensities of theoretical ions, and/or the magnitudes of the mass errors (the difference between theoretical and observed mass-over-charge values).

The computer system generally chooses the explanation with the highest score as the identification for the spectrum. In some embodiments, post-scoring filters are applied to reject certain identifications, for example, based on other channels of information, such as chromatographic retention time. Spectrum identifications can then be integrated into protein identifications by: counting the number of peptide identifications for each protein, counting the total scores of all peptide identifications for each protein, using various other algorithms used in software programs such as Protein-Prophet (from the Institute for Systems Biology in Seattle, Wash.), Scaffold (from Proteome Software, Inc., of Portland, Oreg.), and PROVALT (as described by Weatherly et al., in Mol. Cell. *Proteomics* vol. 4, p. 762, June, 2005).

Spectrum identifications including wild-card modifications can be integrated into higher-level modification information. For example, if a statistically significant number of identifications include a wild-card modification of [+26 Daltons] at or near the N-terminal residue of a peptide, then the computer system may determine that the protein sample appears to have acetaldehyde modification at the N-terminus of peptides. Similarly, if a large number of identifications include a wild-card modification of [+62 Daltons], then the computer system may determine that the protein sample appears to have copper-ion adducts.

Figure 3:
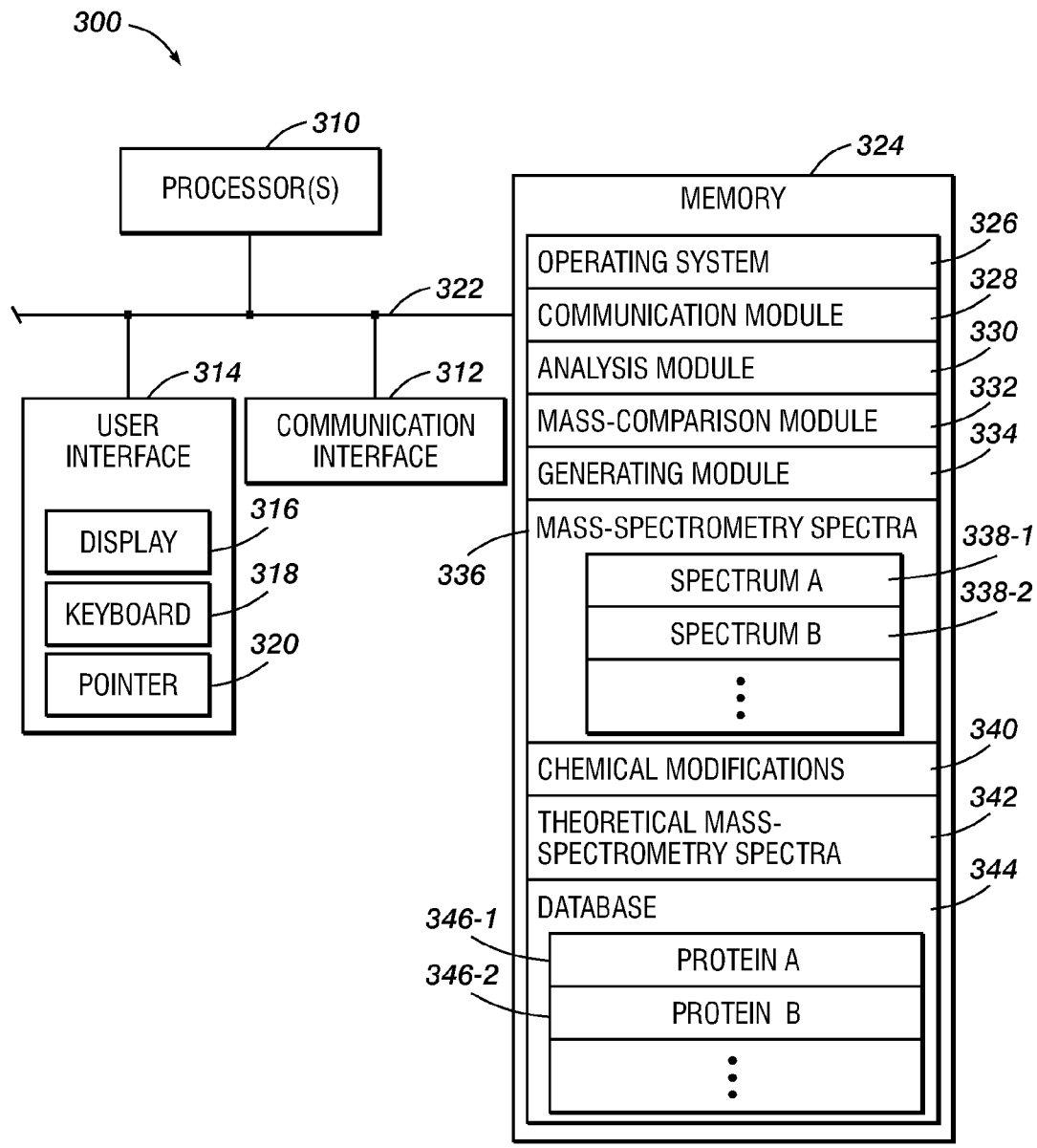
FIG. 3 is a block diagram illustrating a computer system in accordance with an embodiment of the present invention.

We now describe embodiments of a computer system that performs process 200. FIG. 3 presents a block diagram illustrating a computer system 300. Computer system 300 includes one or more processors 310, a communication interface 312, a user interface 314, and one or more signal lines 322 coupling these components together. Note that the one or more processing units 310 may support parallel processing and/or multi-threaded operation, the communication interface 312 may have a persistent communication connection, and the one or more signal lines 322 may constitute a communication bus. Moreover, the user interface 314 may include: a display 316, a keyboard 318, and/or a pointer 320, such as a mouse.

Memory 324 in the computer system 300 may include volatile memory and/or non-volatile memory. More specifically, memory 324 may include: ROM, RAM, EPROM, EEPROM, flash, one or more smart cards, one or more magnetic disc storage devices, and/or one or more optical storage devices. Memory 324 may store an operating system 326 that includes procedures (or a set of instructions) for handling various basic system services for performing hardware-dependent tasks. In some embodiments, the operating system 326 is a real-time operating system. Memory 324 may also store communication procedures (or a set of instructions) in a communication module 328. These communication procedures may be used for communicating with one or more computers, devices and/or servers, including computers, devices and/or servers that are remotely located with respect to the computer system 300.

Memory 324 may also include multiple program modules (or a set of instructions), including: analysis module 330 (or a set of instructions), mass-comparison module 332 (or a set of instructions) and/or generating module 334 (or a set of instructions). Analysis module 330 may identify a best match between a total mass and a mass-spectrometry spectrum for a known protein (such as protein A 346-1 or protein B 346-2) in database 344 and a measured mass-spectrometry spectrum for a protein being analyzed (such as mass-spectrometry spectrum A 338-1 or mass-spectrometry spectrum B 338-2 in mass-spectrometry spectra 336). Note that database 344 may include approximately 20,000,000 peptide combinations (assuming only peptides having a length of 10-30 amino acids).

This identification process may include a known search, a blind search and/or a wild-card-modification search. For example, in a wild-card-modification search, mass-comparison module 332 may determine a maximum mass difference between a known protein and one of mass-spectrometry spectra 336 (such as mass-spectrometry spectrum A 338-1). Then, generating module 334 may generate a set of theoretical mass-spectrometry spectra 342 based on one or more chemical modifications 340 that may be included in the protein being analyzed. Next, analysis module 330 may identify the optimal shift of appropriate peak locations in mass-spectrometry spectrum A 338-1 by comparing the set of theoretical mass-spectrometry spectra 342 with mass-spectrometry spectrum A 338-1. This wild-card-modification search technique may be iterated multiple times for additional chemical modifications 340 until the optimal group of chemical modifications in the peptide or protein sample being analyzed is determined, which may allow the peptide or protein in database 344 with the best match to be identified.

Instructions in the various modules in memory 324 may be implemented in: a high-level procedural language, an object-oriented programming language, and/or in an assembly or machine language. This programming language may be compiled or interpreted, i.e., configurable or configured, to be executed by the one or more processing units 310.

Although computer system 300 is illustrated as having a number of discrete items, FIG. 3 is intended to be a functional description of the various features that may be present in computer system 300 rather than a structural schematic of the embodiments described herein. In practice, and as recognized by those of ordinary skill in the art, the functions of the computer system 300 may be distributed over a large number of devices or computers, with various groups of the devices or computers performing particular subsets of the functions. In some embodiments, some or all of the functionality of computer system 300 may be implemented in one or more application-specific integrated circuits (ASICs) and/or one or more digital signal processors (DSPs).

In some embodiments, computer system 300 includes fewer or additional components. Moreover, two or more components may be combined into a single component, and/or a position of one or more components may be changed. Moreover, the functionality of computer system 300 may be implemented more in hardware and less in software, or less in hardware and more in software, as is known in the art.

Figure 4:
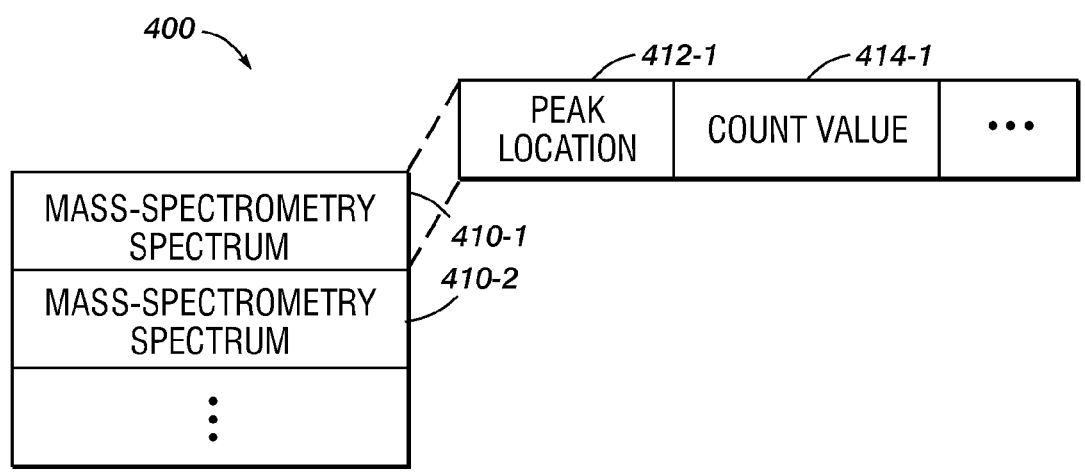
FIG. 4 is a block diagram illustrating a data structure in accordance with an embodiment of the present invention.

We now discuss data structures that may be used in computer system 300. FIG. 4 presents a block diagram illustrating a data structure 400. This data structure may contain mass-spectrometry spectra 410. For example, mass-spectrometry spectrum 410-1 may include multiple pairs of peak locations and corresponding count values, such as peak location 412-1 and count value 414-1.

In some embodiments, data structure 400 includes fewer or additional components. Moreover, two or more components may be combined into a single component, and/or a position of one or more components may be changed.

While the preceding embodiments illustrate the use of the analysis technique in identifying one or more potential chemical modifications to peptides associated with a protein, in other embodiments the analysis technique may be used to analyze mass-spectrometry data associated with a wide variety of materials and chemical compounds, such as macromolecules that are made up of molecular subunits which are bound together at cleavage sites.

The foregoing descriptions of embodiments of the present invention have been presented for purposes of illustration and description only. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

What is claimed is:

1. A method for identifying potential modifications to peptides associated with a precursor peptide, comprising:
   receiving a set of tandem-mass-spectrometry data associated with the precursor peptide, wherein the received spectral data indicates a measured mass for the precursor peptide and a number of peak locations;
   accessing, by one or more computers, a peptide or protein database to obtain spectral information for candidate peptides;
   generating, by one ore more computers, multiple theoretical spectra for the candidate peptides using the spectral information, wherein generating multiple theoretical spectra for a respective candidate peptide involves:
      identifying one or more known mass modifications for the candidate peptide;
      determining at least one variable mass modification to at least one amino acid within the candidate peptide;
      varying the variable mass modification within a predetermined range to produce a set of varied mass modifications; and
      for each varied mass modification, generating a modified theoretical spectrum for the candidate peptide by combining the known mass modifications and the variable mass modification; and
      identifying the potential modifications by comparing the peak locations of the received spectral data with peak locations of each modified theoretical spectrum in the generated theoretical spectra.

2. The method of claim 1, wherein the variable mass modification corresponds to mass values which are unknown prior to identification.

3. The method of claim 2, wherein the variable mass modification comprises a range of mass-value shifts from a minimum shift to a maximum shift.

4. The method of claim 2, wherein the range of values includes positive or negative integers.

5. The method of claim 2, wherein the range of values includes positive or negative non-integer numbers.

6. The method of claim 2, wherein the variable mass modification is associated with particular amino-acid residues in the candidate peptide.

7. The method of claim 2, wherein the variable mass modification is associated with particular amino-acid residue positions in the candidate peptide.

8. The method of claim 2, wherein shifts associated with the variable mass modification includes an uncertainty in the measured mass of the precursor peptide.

9. The method of claim 1, wherein the known mass modifications are associated with a known mass shift prior to identification.

10. The method of claim 1, wherein generating the modified theoretical spectrum further comprising shifting peak locations of fragments containing the at least one amino acid based on the variable mass modification.

11. The method of claim 1, wherein the known mass modifications include: methylation, dimethylation, oxidation, deamidation, carbamylation, phosphorylation or acetylation.

12. The method of claim 1, wherein identifying the potential modifications involves an iterative process, in which variable mass modifications identified in a given iteration are treated as known modifications in a subsequent iteration.

13. The method of claim 1, wherein the predetermined range of the variable mass modification corresponds to a maximum mass difference between the measured mass of the precursor mass and a theoretical mass of the candidate peptide.

14. The method of claim 13, further comprising determining characteristics of one or more candidate peptides corresponding to the precursor peptide prior to determining the maximum mass difference.

15. A computer-program product for use in conjunction with a computer system, the computer-program product comprising a non-transitory computer-readable storage medium and a computer-program mechanism embedded therein for identifying potential modifications to peptides associated with a precursor peptide, the computer-program mechanism including:
  instructions for receiving a set of tandem-mass-spectrometry data associated with a precursor peptide, wherein the received spectral data indicates a measured mass for the precursor peptide and a number of peak locations;
  instructions for accessing a peptide or protein database to obtain spectral information for candidate peptides;
  instructions for generating theoretical spectra for the candidate peptides using the spectral information, wherein generating multiple theoretical spectra for a respective candidate peptide involves:
    identifying one or more known mass modifications for the candidate peptide;
    determining at least one variable mass modification to at least one amino acid within the candidate peptide;
    varying the variable mass modification within a predetermined range to produce a set of varied mass modifications; and
    for each varied mass modification, generating a modified theoretical spectrum for the candidate peptide by combining the known mass modifications and the variable mass modification; and
  instructions for identifying the potential modifications to a candidate peptide by comparing the peak locations of the received spectral data with peak locations of each modified theoretical spectrum in the generated theoretical spectra.

16. The computer-program product of claim 15, wherein the variable mass modification corresponds to mass values which are unknown prior to identification.

17. The computer-program product of claim 16, wherein the variable mass modification comprises a range of mass-value shifts from a minimum shift to a maximum shift.

18. The computer-program product of claim 15, wherein the known mass modifications are associated with a known mass shift prior to identification.

19. The computer-program product of claim 16, wherein identifying the potential modifications involves an iterative process, in which variable mass modifications identified in a given iteration are treated as known modifications in a subsequent iteration.

20. A computer system, comprising:
  a processor;
  memory; and
  a program module, wherein the program module is stored in the memory and configured to be executed by the processor, wherein the program module is for identifying potential modifications to peptides associated with a precursor peptide, the program module including:
  instructions for receiving a set of tandem-mass-spectrometry data associated with a precursor peptide, wherein the received spectral data indicates a measured mass for the precursor peptide and a number of peak locations;
  instructions for accessing a peptide or protein database to obtain spectral information for candidate peptides;
  instructions for generating theoretical spectra for the candidate peptides using the spectral information, wherein generating multiple theoretical spectra for a respective candidate peptide involves:
    identifying one or more known mass modifications for the candidate peptide;
    determining at least one variable mass modification to at least one amino acid within the candidate peptide;
    varying the variable mass modification within a predetermined range to produce a set of varied mass modifications; and
    for each varied mass modification, generating a modified theoretical spectrum for the candidate peptide by combining the known mass modifications and the variable mass modification; and
  instructions for identifying the potential modifications to a candidate peptide by comparing the peak locations of the received spectral data with peak locations of each modified theoretical spectrum in the generated theoretical spectra.

* * * * *

UNITED STATES PATENT AND TRADEMARK OFFICE
CERTIFICATE OF CORRECTION

PATENT NO.         : 9,671,408 B2                                Page 1 of 1
APPLICATION NO.    : 12/272973
DATED              : June 6, 2017
INVENTOR(S)        : Marshall W. Bern It is certified that error appears in the above-identified patent and that said Letters Patent is hereby corrected as shown below:

In the Claims

Column 12, Line 26 please replace the word "ore" with "or"

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*